United States Patent [19]

Fried

[11] Patent Number: 4,962,226

[45] Date of Patent: * Oct. 9, 1990

[54] PROCESS FOR THE SELECTIVE SEPARATION OF VINYLIDENE OLEFINS FROM MIXTURES WITH OTHER OLEFINS

[75] Inventor: Herbert Elliott Fried, Houston, Tex.

[73] Assignee: Shell Oil Company, Houston, Tex.

[*] Notice: The portion of the term of this patent subsequent to Apr. 18, 2006 has been disclaimed.

[21] Appl. No.: 321,117

[22] Filed: Mar. 9, 1989

Related U.S. Application Data

[63] Continuation-in-part of Ser. No. 101,317, Sep. 25, 1987, Pat. No. 4,822,911, which is a continuation-in-part of Ser. No. 812,417, Dec. 23, 1985, abandoned.

[51] Int. Cl.$^5$ .............................................. C07C 69/52
[52] U.S. Cl. .................................................... 560/205
[58] Field of Search ......................................... 560/205

[56] References Cited

U.S. PATENT DOCUMENTS 4,506,095  3/1985  Koermer ............................. 560/205
4,822,911  4/1989  Fried .................................. 560/205

*Primary Examiner*—Paul J. Killos

[57] ABSTRACT

A process for the selective separation of certain vinylidene olefins from their mixtures with linear olefins and for the preparation of valuable alkyl esters of acrylic acid, which comprises steps for (a) contacting and reacting a liquid phase $C_6$ to $C_{30}$ olefin feedstock mixture containing both one or more ethyl- and higher alkyl-branched vinylidene olefins and one or more linear olefins with one or more reactive agents selected from the group consisting of alkyl esters of acrylic acid at a temperature of between about 10 and 300° C. and in the presence of a catalytically effective amount of one or more ene reaction catalysts, to selectively convert all or part of the ethyl- and higher alkyl-branched vinylidene olefins of said feedstock mixture to higher carbon number acrylic acid esters and to produce a product mixture comprising the resulting higher acrylic acid esters and unreacted olefins, and (b) terminating step (a) and separating the unreacted olefins from said product mixture.

The process is of particular benefit in the separation of mixtures of vinylidene olefins and linear alpha-olefins which result from processes for the preparation of higher olefins by the oligomerization of ethylene.

32 Claims, No Drawings

PROCESS FOR THE SELECTIVE SEPARATION OF VINYLIDENE OLEFINS FROM MIXTURES WITH OTHER OLEFINS

This is a continuation-in-part of application Ser. No. 101,317, filed Sept. 25, 1987 U.S. Pat. No. 4,822,911, which is a continuation-in-part of application Ser. No. 812,417, filed Dec. 23, 1985, now abandoned.

BACKGROUND OF THE INVENTION

This invention relates to a process for the treatment of a mixed olefin feedstock, consisting essentially of a specifically defined vinylidene olefin component and a linear olefin component, to accomplish a selective separation between the two components and also a conversion of the vinylidene olefins to a valuable ester product.

The higher carbon number, e.g., $C_6$ and higher, olefins are valuable commodity chemicals having a wide variety of end uses, including, for example, use in the preparation of olefin sulfonate surfactants, plasticizer alcohols, "detergent" alcohols and their derivatives such as alcohol ethoxylate surfactants, and synthetic lubricants. In commercial practice, these olefins are often obtained as mixtures of compounds having different molecular structures. For many applications of the olefins it is recognized to be important to separate such mixtures into components of like structure.

Of particular interest to the present invention is a separation of mixtures containing certain vinylidene olefins, e.g., compounds of the formula

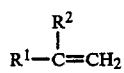

(I)

wherein $R^1$ and $R^2$ each represent an alkyl group. Conventional processes for the preparation of olefins from ethylene via chain growth on aluminum using Zeigler chemistry can result in mixtures of olefins containing substantial amounts of the vinylidene component. Vinylidene olefins are also found, although in lesser quantities, in olefin products synthesized from ethylene by other means, as well as olefins from other sources such as the thermal cracking of higher paraffins. It is recognized in the art (as described, for instance, in U.S. Pat. No. 3,557,236, and U.S. Pat. No. 3,686,250) to be beneficial in many instances to upgrade olefin mixtures to separate the vinylidene components of olefin products from their non-vinylidene components.

Because of similarities between the various olefin structural isomers in terms of boiling points, solubilities, and many other properties, it is generally not practical to separate olefins of like carbon number but different molecular structure using distillation, extraction, or other common separation techniques. This is particularly true of the higher carbon number olefins which are typically manufactured as mixtures of several carbon numbers. It has been proposed in the prior art (U.S. Pat. No. 4,511,753) to selectively remove vinylidene olefins from non-vinylidene olefins by contacting their mixtures with hydrogen sulfide or a hydrocarbyl mercaptan to convert only the vinylidene olefins to corresponding sulfides, and subsequently separating the non-vinylidene olefins from the sulfided mixture. Conversely, U.S. Pat. No. 3,291,853 discloses the selective conversion of linear alpha-olefins (olefins of formula I, wherein $R^1$ is alkyl and $R^2$ is hydrogen) from mixtures with vinylidene olefins upon contact with aluminum alkyls.

Also of substantial value in the chemical industries are higher carbon number, e.g., $C_9$ and higher, carboxylic acid alkyl esters, which are known to find use, for example, in formulating medicines, ointments, cosmetics, and lubricating oils, as soaps, and as intermediates in the preparation of metal (e.g., aluminum or zinc) salts.

In one important respect, the present invention provides a process for a separation between certain vinylidene olefins and other olefinic compounds, which comprises a step for the contact of the mixture with a reactive agent selected from the group consisting of the alkyl esters of acrylic acid (for example, methyl acrylate), in the presence of an "ene" reaction catalyst. In the course of this step, the reactive agent converts the vinylidene olefin component to corresponding unsaturated alkyl esters. In general, the addition reaction of a vinylidene olefin (I) with an alkyl ester of acrylic acid (II) for preparation of a higher carbon number ester product (III) can be represented by the equation

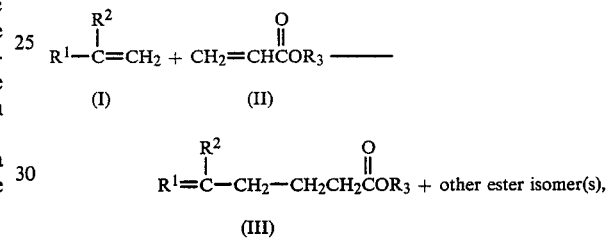

wherein $R^1$ and $R^2$ are as defined above for formula I, and $R^3$ is alkyl. The specific higher ester product III in the equation is one of the isomers of such esters which result from the reaction. In the practice of the invention, this conversion to higher esters is highly selective for the vinylidene component. The reaction is found to be selective, in the sense that essentially all of a certain class of the vinylidene compounds can be converted, without significant conversion of the remainder of the compounds in the mixture. Prior art relevant to such a reaction step includes disclosures such as those of U.S. Pat. No. 3,783,136 which describes a process utilizing a catalyst of the form $AlX_3$, where X is chlorine or bromine, to convert olefins, including linear alpha-olefins, to unsaturated mono- and di- carboxylic acid esters, and the similar process of U.S. Pat. No. 3,641,120 which utilizes a manganic carboxylic acid salt or oxide catalyst. In a later publication in J. Org. Chem., Vol. 39 (1974), No. 2, pp. 255–256, B. R. Snider reports that only 1,1-disubstituted (i.e., vinylidene) olefins are reactive in certain ene reactions, and that ene reaction products were not obtained with such olefins as 1-octene and cyclohexene. Snider does not report, however, any reaction of any vinylidene olefins in the presence of non-vinylidene olefins. The publication of A. Akermark and A. Ljungqvist, in J. Org. Chem., Vol. 43 (1978), No. 22, pp. 4387–4388, reports that Snider did not observe a conversion of 1-octene and like linear olefins because of an isomerization reaction which converted the linear olefin reactant to an internally-substituted reactant which then formed branched products. Using a modified catalyst, Akermark et al obtained a 40% conversion of 1-octene with methyl acrylate. Again, the reference fails to disclose a reaction involving a mixed, vinylidene and non-vinylidene olefins, and the high conversion of the linear alpha-olefin reported by Akermark et al as well as by the aforementioned patents is not suggestive of a separation process in which linear olefins are essentially unreactive. C. J. Albisetti et al (J. Amer. Chem. Soc., Vol. 78 (1956), pp. 2637-2641) also describe various reactions of either vinylidene or non-vinylidene olefins with methyl acrylate and the like.

SUMMARY OF THE INVENTION

It has now been found that a certain class of vinylidene olefins can be removed from mixtures with linear olefins in a process in which the mixture is contacted and, at least in part, reacted with an agent selected from the group consisting of the alkyl esters of acrylic acid and mixtures thereof, in the presence of an ene reaction catalyst.

It is critical to this process that the vinylidene olefins of the mixture consist essentially of ethyl- and higher alkyl-branched vinylidene olefins. (The class of olefins described by formula I above wherein each of the $R^1$ and $R^2$ substituents has two or more carbon atoms is herein referred to as the class of "ethyl- and higher alkyl-branched" vinylidene olefins.) Contact of the olefin mixture with acrylate ester(s) in the presence of the catalyst results in a selective conversion of the ethyl- and higher alkyl-branched vinylidene olefins of the mixture. Under the invention, this conversion takes place without significant conversion of the linear (i.e., straight chain) olefin component of the mixture. This process is thus capable of both producing a higher ester product which derives solely from the particular ethyl- and higher alkyl-branched vinylidene olefins while leaving an upgraded olefin product in which the content of ethyl- and higher alkyl-branched vinylidene olefins is reduced or, if desired, substantially eliminated.

In addition, the process of the invention further comprises a step for the termination of the contact/reaction step involving the ethyl-and higher alkyl-branched vinylidene olefins, prior to the onset of any substantial reaction of the linear olefins present with the reactive agent and for the separation of the unconverted olefins from the product esters, by distillation, extraction, or the like.

It is considered surprising that the process of the invention is highly selective for the conversion and separation of only the ethyl- and higher branched vinylidene olefin content of a mixture containing linearolefins. On the one hand, under practice according to the invention, linear olefins are found to be essentially unreactive when contact with the specified reactive agent takes place in the presence of ethyl- and higher alkyl-branched vinylidene olefins. On the other hand, these same linear olefins are significantly reactive with the indicated alkyl ester reactive agent when such contact takes place in the absence of ethyl- and higher alkyl-branched vinylidene olefins. Moreover, it is also considered surprising that the ethyl- and higher alkyl-branched vinylidene olefins can be selectively converted and separated in the process at conditions under which corresponding methyl-branched vinylidene olefins (compounds of formula I, wherein $R^1$ and R2 are both alkyl and at least one of $R^1$ and $R^2$ is methyl) do not selectively react with the same reactive agents.

Accordingly, the present invention can be described in brief summary as a process for the separation of an olefin mixture consisting essentially of an ethyl- and higher alkyl-branched vinylidene olefins component and a linear olefin component, which comprises steps for (a) contacting and reacting the olefin mixture in the liquid phase at a temperature of between about 10° and 300° C. with one or more reactive agents selected from the group consisting of alkyl esters of acrylic acid in the presence of a catalytically effective amount of one or more ene reaction catalysts, to selectively convert all or part of the ethyl- and higher alkyl-branched vinylidene olefins of said olefin mixture to higher carbon number acrylic acid esters and to produce a product mixture comprising the resulting higher acrylic acid esters and unreacted olefins, (b) terminating step (a) and separating the unreacted olefins from said product mixture.

The invention has advantage from the standpoint of separating the ethyl- and higher alkyl-branched vinylidene olefin component from the mixture, of upgrading the linear olefin, and of preparing the valuable ester derivatives of the vinylidene olefins.

In commercial practice, the invention is of particular advantage in application to the separation of ethyl- and higher alkyl-branched vinylidene olefins from mixtures in which the linear olefin component consists essentially of linear alpha-olefins.

DESCRIPTION OF THE PREFERRED EMBODIMENTS

The invention is suitably applied to the separation of olefin mixtures having a vinylidene olefin component consisting essentially of an ethyl- and/or higher alkyl-branched vinylidene olefin component and a linear olefin component consisting of linear alpha- and/or internal mono-olefins.

The olefin mixture to which the invention is applied is to be understood to consist essentially of the ethyl- and higher alkyl-branched vinylidene olefins in the sense that it does not contain significant amounts (e.g., that it contains less than about 10% w, preferably less than about 5% w and most preferably less than about 3% w, relative to the weight of the mixture) of other olefinic compounds. The mixture may, however, suitably contain other, non-olefinic components (e.g., paraffins) which are essentially inert under process operating conditions.

It is particularly important that the vinylidene olefin component of the mixture consist essentially of aliphatic mono-olefins of formula I above wherein both $R^1$ and $R^2$ have at least two carbon atoms each, and may contain at most only small quantities (i.e., less than 5 percent by weight (% w), preferably less than 3% w, and most preferably less than 2% w, relative to the weight of the ethyl- and higher alkyl-branched vinylidene olefins) of "methyl-branched" vinylidene olefins, which can be represented by formula I above with $R^1$ and $R^2$ both representing alkyl groups and at least one of the $R^1$ and $R^2$ groups representing a methyl group.

It has been found that, under the operating conditions of this invention, methyl-branched olefins react with themselves to form oligomers and with the other components of the contact mixture to produce a variety of by-products, which include, for example, esters of higher olefin oligomers. It is for this reason that the application of this invention is considered to be limited to olefin mixtures having a vinylidene olefin component which consists essentially of ethyl- and higher alkyl-branched vinylidene olefins, and is essentially free of methyl-branched vinylidene olefins.

From the standpoint of its commercial utility, the invention is particularly applicable to mixtures wherein the linear olefin component consists predominantly of linear alpha-olefins. That is, at least about 75% w, preferably at least about 90% w, and most preferably at least about 95% w of the linear olefins are alpha-olefins rather than internal olefins. However, the linear olefin component may very suitably comprise, or even consist essentially of, linear internal olefins.

Commercially prepared olefin mixtures to which the invention is very suitably applied are exemplified by products having a molar ratio of linear olefins to ethyl- and higher alkyl-branched vinylidene olefins which is in the range from about 2:1 to 100:1. The invention is considered to have most practical application in the separation of olefin mixtures which have a molar ratio of linear olefins to ethyl- and higher alkyl-branched vinylidene olefins in the range from about 3:1 to 20:1.

In terms of the carbon number of the olefins of the mixture, the invention is preferably applied to the separation of mixtures of olefins wherein both of the olefin components have carbon number(s) in the range from 6 to about 30, more preferably to the separation of mixtures of olefins for which both components have carbon number(s) in the range from about 10 to 20, and most preferably to the separation of olefins having carbon number(s) in the range from about 14 to 18. The invention is applied to best advantage in the separation of olefin mixtures wherein the carbon number distribution of the ethyl- and higher alkyl-branched vinylidene olefin component overlaps that of the linear olefin component, i.e., cases in which both the ethyl- and higher alkyl-branched vinylidene component and the linear olefin component contain olefins of the same carbon number. Most preferably, the invention is applied to olefin mixtures characterized by a range of different carbon number molecules and by a carbon number distribution for the ethyl- and higher alkyl-branched vinylidene olefins is substantially the same as the carbon number distribution for the linear olefins. It is in such cases that these olefin mixtures are most difficult to separate in conventional fashion, e.g., by direct distillation or extraction or the like.

For purposes of the process of this invention, the olefin mixture is contacted, in the presence of an ene reaction catalyst, with a reactive agent selected from the group consisting of the alkyl esters of acrylic acid (alkyl acrylate esters) and mixtures thereof. As a result of this contact, the ethyl- and higher alkyl-branched vinylidene olefins of the mixture undergo reaction with the acrylate esters and are in whole or in part converted to higher ester adducts. The class of alkyl esters of acrylic acid which is suitable for use as reactive separation agent in the process of the invention is to be understood to include acrylates and alkyl-substituted acrylates which can be represented by the formula

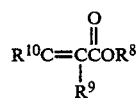

wherein $R^8$ is an alkyl group, preferably an alkyl group having a carbon number in the range from 1 to about 30, and $R^9$ and $R^{10}$ each independently represent either a hydrogen atom or an alkyl group. If desired, the acrylate ester reactive agent may be suitably substituted with one or more substituents (for example, chlorine or other halogen atom(s)), which do not substantially affect the intended conversion and separation.

Preferences can be expressed for use as an acrylate ester reactive agent in the invention of alkyl esters of acrylic acid corresponding to the above formula wherein the alkyl substituent $R^8$ has from 1 to about 15 carbon atoms, more preferably from 1 to about 8 carbon atoms, and is most preferably methyl, wherein the $R^9$ substituent is hydrogen or $C_1$ to $C_4$ alkyl, more preferably hydrogen, and wherein the $R^{10}$ substituent is hydrogen or $C_1$ to $C_{18}$ alkyl, more preferably hydrogen or $C_1$ to $C_4$ alkyl, and most preferably hydrogen. Specific examples of such alkyl esters include those of the group consisting of methyl acrylate, ethyl acrylate, n-propyl acrylate, isopropyl acrylate, n-butyl acrylate, isobutyl acrylate, tertiary-butyl acrylate, n-octyl acrylate, isooctyl acrylate, 2-ethylhexyl acrylate, n-tetradecyl acrylate, n-hexadecyl acrylate, and methyl alpha-chloroacrylate. In one respect, the lower acrylate esters, particularly those having from four to about 8 total carbon atoms, and most particularly those for which the $R^9$ and $R^{10}$ substituents are hydrogen, are a preferred class of reactive agents for most applications of the invention. Very good results have been obtained using methyl acrylate. In another respect, the higher alkyl esters, particularly those having a total of from about 8 to 15 carbon atoms, may be preferred for the use in the separation of olefin mixtures having a relatively broad carbon number distribution. As an illustration, it may be beneficial to make use of such higher carbon number alkyl ester reactive agents in order to insure that the higher acrylate ester adducts of the vinylidene olefins will have a boiling point significantly greater than that of the linear olefins in the mixture, so that they can be more effectively separated by distillation in the subsequent olefin recovery step.

Also suitable as the reactive agent in the process of the invention are dimers, trimers and other oligomers of the indicated acrylic acid esters, such as, for example, trimethylolpropane triacrylate, 1,6-hexanediol diacrylate.

The step for contact of the olefin mixture with the reactive agent and the conversion, in whole or in part, of the mixture's ethyl- and higher alkyl-branched olefins to higher acrylate ester adducts of the vinylidene olefins is necessarily carried out in the presence of an "ene" reaction catalyst. The choice of the particular ene reaction catalyst suitable for use in this invention has not been found to be a critical aspect of the invention. Conventional ene reaction catalysts are generally suitable, and are known, for instance, from the disclosures of U.S. Pat. No. 3,783,136 and the above cited publications, to particularly include aluminum chloride, aluminum bromide, and mixtures of aluminum chloride with other inorganic salts such as NaCl and KCl. Alkali metal tetrachloroaluminates (e.g., $CsAlCl_4$, $KAlCl_4$, and $LiAlCl_4$), alkylaluminum chlorides such as ethylaluminum chloride $(C_2H_5AlCl_2)$, gallium chloride, tantalum pentachloride, indium chloride, and catalysts combining aluminum chloride and transition metal sulfate salts, for example, copper, nickel and iron salts have also been observed to be useful. The class of ene reaction catalysts consisting of aluminum chloride, indium chloride, and the lower alkyl (e.g., $C_1$ to $C_4$) aluminum dichlorides is considered particularly preferred for use in the invention. Best results have been obtained using a lower alkyl aluminum chloride, specifically ethyl aluminum dichloride.

For purposes of the practice of the invention, the mixture of vinylidene and linear olefins is contacted with the reactive agent in the presence of the specified catalyst. The relative proportions of the reactive agent utilized in this contact are not critical to the invention. However, in order to accomplish a substantially complete separation between the vinylidene and linear olefin components, preferred embodiments of the invention generally employ a number of moles of reactive agent in this contact which equals or exceeds the number of moles of vinylidene olefins. Preferably, the molar ratio of the reactive agent to the ethyl- and higher alkyl-branched vinylidene component of the olefin mixture is between about 0.5:1 and 10:1, and more preferably is between about 1:1 and 5:1. However, the process can be practiced with a lesser relative proportion of the reactive agent if conversion and separation of less than all of the vinylidene olefin is desired. A 1:1 ratio of reactive agent to vinylidene olefin is typically sufficient for conversion of substantially all of the vinylidene olefin. Limiting the molar ratio of reactive agent to vinylidene olefin to about 1:1 is also preferred as a means both of discontinuing the contact and reaction step at a point prior to significant conversion of the linear olefin component of the mixture and of minimizing the recovery from the product of excess and unreacted acrylate reactive agent.

The ene reaction catalyst is suitably present in the contact/reaction step in a catalytically effective amount. Although the exact quantity of catalyst which is necessary will vary from one suitable catalyst to another, quantities between about 0.01 and 30% w, based on the olefin mixture) are typically suitable. Catalyst quantities in the range of from about 0.5 to 10.0% w are preferred, while quantities in the range of from about 2 to 5% w are considered most preferred.

In addition to the ene catalyst, it has been found useful to add to the reaction mixture a small quantity of a material such as hydroquinone, in order to inhibit free-radical catalyzed polymerization reactions involving the reactive agent.

It is considered critical to the invention that the step of the process for contact and reaction of the olefin mixture with the acrylate ester reactive agent be carried out at a temperature of at least about 10° C. However, it is only at elevated temperature, e.g., about 40° C. or greater, or in the presence of a solvent, that the process of the invention achieves the desired conversion of the ethyl- and higher alkyl branched vinylidene olefin at a significant rate. The separation process remains selective at temperatures up to about 300° C., and possibly higher. However, at temperatures above 300° C., the process encounters substantial side reactions and produces, for instance, undesirable levels of olefin dimers. Thus, the process of the invention is most suitably carried out at a temperature in this reaction step which is in the range from about 40° to 300° C. From the standpoint of reducing dimerization and other side reactions, preference can be expressed for a temperature of no greater than about 275, particularly a temperature no greater than about 250° C. Overall the reaction temperature is preferably in the range from about 40° to 275° C., more preferably in the range from about 40° to 250° C., and most preferably in the range from about 50° to 200° C. Particularly good performance is obtained at a temperature in the range from about 60° to 150° C., while a temperature in the range from about 80° to 120° C. is generally considered optimal from the standpoint of both the selectivity and the rate of the vinylidene olefin conversion.

Pressure has not been found to be a critical aspect of this process step, although it is intended that the pressure be sufficient to maintain the vinylidene and linear olefin components of the olefin mixture and the reactive agent substantially in the liquid phase. Operation at a pressure between about 0 and 1000 psig has been found to be very convenient. Higher pressures, e.g., 2000 psig or greater, are also considered suitable.

The contact/reaction step is suitably carried out in the presence of solvents such as benzene, toluene, and other solvents which are recognized in the art for service in ene reactions. However, it is strongly preferred that the step be conducted in the absence of any substantial amount of any such solvent. Experience with the practice of the invention has generally shown solvents to be of disadvantage because they reduce throughput in the reactor, require removal from the product, interfere with catalyst removal from the product, and increase the potential for formation of by-products in the reaction.

In the course of the contact/reaction step at least a portion of the ethyl- and higher alkyl-branched vinylidene olefins in the olefin mixture is converted to unsaturated higher carbon number acrylic acid esters. The linear olefins are essentially unreactive in this step, that is, at least until substantially all of either the vinylidene olefin or the reactive agent has been depleted. In effect, the vinylidene olefins and the linear olefins react in a sequential or step-wise fashion—the vinylidene olefins react until substantially depleted, at which point there commences a reaction between the linear olefins and remaining reactive agent. In the practice of this invention, advantage is taken of this sequential or step-wise reaction of, first, the vinylidene olefins and, second, the linear olefins to provide a selective separation of one olefin component of the feedstock mixture from the other. For this purpose, it is necessary to terminate the reaction of the reactive agent with the olefin mixture before the reaction has run its full course.

The measure of the selectivity of the separation between vinylidene olefins and the linear olefins in the process of the invention is primarily dependent upon the point at which termination of the reaction with acrylate ester reactive agent takes place. It is critical to the process that the contact/reaction step be terminated before the point at which a substantial quantity of the linear olefin fraction is converted to higher carbon number ester. In this respect, the separation process does not accomplish a perfectly selective separation, but is generally considered to be selective so long as the contact/reaction step is terminated before substantial conversion, e.g., conversion of more than about 20%, of the linear olefins. Preferably, the contact/reaction step is terminated before conversion of more than about 10% of the linear olefins of the feedstock mixture. To some extent, the optimum termination point in a given application of the invention will be a function of the desired extent of the removal of the vinylidene olefin component, and a deeper conversion and removal of the vinylidene olefins will require a higher level of conversion of the linear olefins. For example, under preferred practices, the invention is generally capable of achieving at least a 90% conversion and separation of the vinylidene olefins, with an accompanying conversion of the linear olefins which is less than about 10%. Most preferably, the contact/reaction step is terminated before conversion of more than about 5% of the linear olefins to higher carbon number esters.

In many cases, it will be most desirable to continue the practice of the contact/reaction step of the invention through the conversion of substantially all, e.g., at least 80%, of the vinylidene olefins of the feedstock. As a rule, the invention will be of greater value in applications which accomplish more complete separation of the vinylidene olefins to produce both a greater quantity of the higher ester and a higher purity linear olefin product. In this respect, it is more preferable to continue the contact/reaction step through conversion of at least about 90%, more preferably at least about 95%, of the vinylidene olefins. However, it is not critical to the invention that the process be continued to high vinylidene olefin conversion, and the invention may be suitably practiced with termination of the contact/reaction step after only a small conversion of the vinylidene olefin component. Removal of even small portions of vinylidene olefins is generally of advantage from the standpoint of upgrading mixed feedstocks. Moreover, embodiments of the invention wherein a minor portion (e.g., 50% or less) of the vinylidene olefins is converted are typically very highly selective with respect to a minimal conversion of the linear olefins present.

Termination of the contact/reaction step is suitably accomplished by cooling the contact mixture, e.g., to 15° C., and/or by adding a base (for example, an alkali or alkaline earth metal hydroxide) to neutralize and inactivate the ene reaction catalyst. If the contact/reaction step is conducted in the absence of a solvent, cooling of the mixture to room temperature is typically sufficient to effectively terminate the reaction. Cooling to lower temperatures, e.g., 0° C. or below, may be necessary to terminate a reaction carried out in the presence of an added solvent.

Either in the course of or following termination of the reaction, the product mixture is also preferably treated for separation, e.g., by filtration, of the ene reaction catalyst or catalyst residues. In many cases, the catalyst is partially soluble in the product medium. To extract catalyst and catalyst residues from solution, it has also been found useful to wash the mixture with an aqueous acid solution, e.g., with an equal volume of a 1-10% aqueous sulfuric acid solution. In general, catalyst removal is suitably accomplished by methods known in the art for application to ene reaction products.

The contact/reaction step is also very suitably terminated by depletion of the ester reactive agent. For example, if the number of moles of reactive agent utilized is essentially equivalent to the number of moles of vinylidene olefin in the feedstock, the selective reaction will result in essentially complete conversion of the vinylidene olefins without significant conversion of the linear olefins.

The contact/reaction step yields a mixture containing both a higher unsaturated acrylate ester component, comprising the products of the addition reaction between the olefins and the reactive agent, and an olefin component comprising those olefins which have not undergone reaction with the reactive agent. In addition, the product mixture may also contain products of side reactions involving the vinylidene olefins (and to a much lesser extent the linear olefins), such as diesters, dimers, and derivatives of catalyst components, such as chlorinated hydrocarbons (alkyl chlorides).

In the process of this invention, the product mixture is subsequently treated for separation of the two principal components. Recovery from this mixture of olefin which is enriched in its linear olefin component is suitably accomplished by such conventional methods as distillation, solvent extraction or the like. Distillation (including simple evaporation) of the remaining olefins from the higher boiling acrylate ester products of vinylidene olefin conversion is particularly preferred. As will be understood by those skilled in the art, the conditions of temperature and pressure for a particular distillative separation will vary with the carbon numbers of the olefins and the acrylate ester product.

As indicated hereinabove, distillation is most effective for recovery of linear olefins from a contact/reaction step product mixture when there are significant differences between the boiling points of the linear olefins and of the acrylate ester product of the vinylidene olefins. For this reason the invention is particularly useful in application to olefin feedstocks having relatively narrow carbon number distribution, for example, to mixtures in which substantially all (e.9., 90% or more) of the olefins are distributed over no greater than a five carbon number range, such as $C_{10}$ to $C_{14}$ or $C_{14}$ to $C_{18}$. More preferably, the olefin feedstock mixture has a carbon number distribution in which essentially all of the olefins are within a carbon number range no greater than five.

Any unreacted excess of reactive agent which remains in the contact step product mixture may suitably be recovered by a separate distillation, preferably before distillation or other separation of the product acrylate ester/olefin mixture.

The invention is further described by reference to the following examples, which are intended to illustrate certain preferred embodiments and not to limit its broader scope.

EXAMPLE 1

In this example of practice according to the invention, a mixture (totaling 19.75 grams, 0.088 mol) of $C_{16}$ olefins, containing about 24% ethyl- and higher alkyl-branched vinylidene olefins (4.74 grams; 0.021 mol) and about 76% linear olefins (15.01 grams; 0.067 mol)) was contacted with 1.89 grams (0.022 mols) of methyl acrylate. The linear component comprised 14.02 grams of linear alpha- olefin and 0.99 grams of linear internal olefins.

This contact took place in an 80 ml autoclave, at 100° C., under a nitrogen atmosphere, and in the presence of an ene reaction catalyst consisting of 0.0044 mol of ethylaluminum dichloride. In practice, the catalyst was in the form of a 25% w solution in hexane, and 2.24 grams of this solution was added to the contact/reaction mixture. Hydroquinone, in a quantity of 0.05 grams, was also added to the mixture to inhibit free radical polymerization of the methyl acrylate.

After 16 hours of contact and reaction, the product mixture was removed from the autoclave, cooled, and analyzed by gas chromatography/mass spectroscopy methods. The analysis indicated a 15.7% conversion of the olefins, with a selectivity of 92.9w % to the higher mono-ester product, 4.4% w to the diester, and 2.7w % to heavy by-products such as olefin oligomers. The analysis indicated that essentially 100% of the mono-ester products were derived from the vinylidene olefins.

EXAMPLE 2

In this example of practice according to the invention, a mixture (totaling 19.76 grams, 0.088 mol) of $C_{16}$ olefins, containing about 24% ethyl- and higher alkyl-branched vinylidene olefins (4.74 grams; 0.021 mol) and about 76% linear olefins (15.02 grams; 0.067 mol) was contacted with 7.56 grams (0.088 mols) of methyl acrylate. The linear olefin component comprised 14.03 grams of linear alpha-olefin and 0.99 grams of linear internal olefins).

Contact took place in an 80 ml autoclave, at 100° C., under a nitrogen atmosphere, and in the presence of an ene reaction catalyst comprising 0.59 grams of anhydrous aluminum chloride, 0.08 grams of potassium chloride, 0.064 grams of sodium chloride. Hydroquinone (0.05 grams) was also added.

After 16 hours of contact and reaction, the product mixture was removed from the autoclave, cooled, and analyzed by gas chromatography/mass spectroscopy methods. Analysis of the higher alkyl mono-ester product showed that about 96% was a derivative of the vinylidene olefins and only about 3% was a derivative of linear olefins.

The vinylidene olefin conversion product was found to comprise 81.5% of the desired $C_{19}$ unsaturated methyl ester, 4.8% $C_{22}$ unsaturated diesters, and 13.7% saturated $C_{16}$ chlorides, with these percentages calculated on the basis of the total vinylidene olefin which was converted.

COMPARATIVE EXPERIMENTS A AND B

For purposes of comparison, a comparative experiment A not in accordance with the invention was carried out under procedures similar to those of Examples 1 and 2, but using an olefin feedstock which contained only non-vinylidene olefins. This comparative experiment illustrates that non-vinylidene olefins readily react with the specified reactive agent used in the process of the invention, when their contact with the agent takes place in the absence of vinylidene olefins. Specifically, 9.88 grams of $C_{16}$ linear olefins (90+% linear alpha-olefins) was contacted and reacted with 7.58 grams of methyl acrylate for 16 hours at a temperature of 100° C. in the presence of 1.2 grams of ene catalyst (a mixture of 62.6% w aluminum chloride and 37.4% w copper sulfate) and of 0.05 grams of hydroquinone. Analysis of the product indicated a 41.8% conversion of the $C_{16}$ linear olefins, with a selectivity of 76.5% to the mono-esters, of 5.6% to heavier by-products, and of 17.8% to chlorinated hydrocarbons.

In a second comparative experiment, B, a feedstock containing only 1-octene was contacted and reacted with an equimolar quantity of methyl acrylate in the presence of a catalyst containing a mixture of aluminum chloride, potassium chloride, and sodium chloride (respective molar ratios of the catalyst components to olefin feedstock were 0.1:0.025:0.025:1) and of 0.050 grams of hydroquinone. After a 16 hour reaction at 100° C., 29% of the 1-octene had been converted to monoester (selectivity of 81%) or chlorinated hydrocarbons (selectivity of 19%).

EXAMPLE 3

Following the general procedures described for Examples 1 and 2, the same quantity (19.76 grams) of the same $C_{16}$ olefin mixture was contacted with 15.1 grams of methyl acrylate in the presence of a catalyst comprising 0.59 grams of anhydrous aluminum chloride, 0.37 grams of cesium chloride, and also in the presence of 0.05 grams of hydroquinone. The contact took place in the autoclave, at a temperature of 100° C. for a total of 16 hours. Analysis of the final reaction mixture indicated a 96% conversion of the vinylidene olefins.

The product of the vinylidene olefin reaction comprised 86% unsaturated $C_{19}$ methyl ester, 3.8% $C_{22}$ unsaturated diester, and 10% $C_{16}$ saturated chlorides.

EXAMPLE 4

The general procedures were again applied to the contact of the same quantity of the same $C_{16}$ olefin mixture with 7.56 grams of the methyl acrylate reactive agent. In this case, however, the contact between the olefin mixture and the reactive agent was continued beyond the point of essentially complete conversion of the vinylidene olefin in the mixture. The contact was not terminated prior to substantial conversion of the mixture's linear olefin component. In the presence of a catalyst comprising 2.35 grams of anhydrous aluminum chloride, 0.32 grams of potassium chloride, 0.24 grams of sodium chloride, and 0.05 grams of hydroquinone, contact over 5 hours at 100° C. and under nitrogen atmosphere converted not only 100% of the vinylidene component but also 41% of the linear component.

This example shows that the process selectivity to the conversion of only the vinylidene olefin component of the mixture is decreased if contact with reactive agent is continued beyond the point of substantially complete conversion of the linear component.

EXAMPLE 5

An olefin mixture comprising 3.37 grams of 2-hexyl-1-decene (a $C_{16}$ alkyl-branched vinylidene olefin) and 4.88 grams of $C_{12}$ linear alphaolefins was contacted with 4.45 grams of methyl acrylate in the presence of 0.59 grams of anhydrous aluminum chloride, 0.08 grams of potassium chloride, 0.06 grams of sodium chloride, and 0.05 grams of hydroquinone. After 5 hours of contact and reaction at 100° C., 91% of the $C_{16}$ vinylidene olefin was converted to a mixture of $C_{19}$ unsaturated alkyl ester (91% of converted vinylidene olefin), $C_{22}$ unsaturated diester (7% of converted vinylidene olefin), and $C_{32}$ dimer (2% of converted vinylidene olefin). A total of 4.5% of the linear olefin was converted to a $C_{12}$ saturated chloride. Analysis of the product failed to detect any of a $C_{15}$ unsaturated alkyl ester as would have resulted from a reaction of the linear olefin with the methyl acrylate.

EXAMPLE 6

In a one-gallon autoclave under a nitrogen atmosphere, a total of 935 grams (4.17 mols) of a $C_{16}$ olefin mixture was contacted with 89.5 grams (0.83 mol) of methyl acrylate. The olefin mixture contained about 70% linear alpha-olefins, 25% ethyl- and higher alkyl-branched vinylidene olefins, and 5% linear internal olefins. This mixture was contacted and reacted in the presence of 25.8 grams (0.19 mol) of anhydrous aluminum chloride for about 5 hours at 100° C. Total conversion of olefin was 18.3%, with selectivity of 86.3% to the mono-ester, 8.1% to the di-ester, and 5.6% to heavier by-products.

EXAMPLE 7

A typical product mixture resulting from contact and reaction between a $C_{16}$ olefin mixture (24% ethyl- and higher alKyl-branched vinylidene olefins and 76% linear olefins) and methyl acrylate in the presence of an ene reaction catalyst (after catalyst removal by washing with aqueous sulfuric acid) was distilled under vacuum to separate unreacted olefins. The product mixture was subjected to a batch distillation in a 30 tray Oldershaw column. Four cuts were made during distillation: a first cut in a 500°-565° F. normal boiling point range, consisting essentially of linear alpha-olefins; a second cut in a 565°-620° F. normal boiling point range, consisting largely of internal olefins and alkyl chloride by-products; a third cut in a 620°-720° F. normal boiling point range containing the $C_{19}$ unsaturated methyl esters resulting from the reaction of the vinylidene olefins with methyl acrylate; and a fourth cut having a normal boiling point of 720° F. containing heavier by-product materials.

COMPARATIVE EXPERIMENT C

Comparative Experiment C illustrates the nonselective reaction of a methyl-branched vinylidene olefin with methyl acrylate. 2-Methyl-1-pentene (14.9 grams; 0.176 mol) was contacted with methyl acrylate (15.15 grams; 0.176 mol) in the presence of 2.3 grams of aluminum chloride and 0.05 grams of hydroquinone. The contact was continued for approximately 16 hours at a temperature of about 100° C. Analysis indicated that mono- and di-esters of $C_6$ olefin accounted for only about 4% of the product, the remainder being essentially olefin oligomers (e.g., dimers and trimers) and esters of olefin oligomers.

For comparison, the ethyl-branched vinylidene olefin 2-ethyl-1-butene (formula I, with $R^1$ and $R^2$ both ethyl groups) was contacted with methyl acrylate using the same quantities of olefin, reactive agent and catalyst and the same process conditions. The product consisted essentially of mono-esters of the $C_6$ olefin and di-esters of the $C_6$ olefin, in a weight ratio of about 2.3:1.

I claim as my invention:

1. A process for the selective separation of a $C_6$ to $C_{30}$ olefin mixture consisting essentially of an ethyl- and higher alkyl-branched vinylidene olefin component and a linear olefin component, and for the preparation of unsaturated alkyl esters of acrylic acids, which comprises steps for
    (a) contacting the olefin mixture in the liquid phase at a temperature of between about 10° and 300° C. with one or more reactive agents selected from the group consisting of alkyl esters of acrylic acid in the presence of a catalytically effective amount of one or more ene reaction catalysts, to selectively convert all or part of the ethyl- and higher alkyl-branched vinylidene olefins of said mixture to higher alkyl acrylic acid esters and to produce a product mixture comprising the resulting higher acrylic acid esters and unreacted olefins,
    (b) terminating step (a) prior to conversion of more than about 20% of the linear olefins by reaction with reactive agent, and
    (c) separating the unreacted olefins from the product mixture.
2. The process of claim 1, wherein the one or more alkyl esters of acrylic acid of the reactive agent have the formula

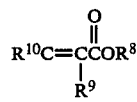

wherein $R^8$ is an alkyl group of from 1 to about 15 carbon atoms, $R^9$ is a hydrogen atom or an alkyl group of from 1 to about 4 carbon atoms, and $R^{10}$ is a hydrogen atom or an alkyl group of from 1 to about 18 carbon atoms.

3. The process of claim 2, wherein the reactive agent comprises one or more alkyl esters of acrylic acid selected from the group consisting of methyl acrylate, ethyl acrylate, n-propyl acrylate, isopropyl acrylate, n-butyl acrylate, isobutyl acrylate, tertiary-butyl acrylate, n-octyl acrylate, isooctyl acrylate, 2-ethylhexyl acrylate, n-tetradecyl acrylate, n-hexadecyl acrylate, methyl alpha-chloroacrylate, trimethylolpropane triacrylate, 1,6-hexanediol diacrylate, and mixtures thereof.

4. The process of claim 3, wherein the reactive agent is methyl acrylate.

5. The process of claim 1, wherein the olefin mixture contains one or more ethyl- and higher alkyl-branched vinylidene olefins having carbon numbers in the range from about 10 to 20 and one or more linear olefins having carbon numbers in the range from about 10 to 20.

6. The process of claim 5, wherein the linear olefins are in major part linear alpha-olefins.

7. The process of claim 6, wherein the linear olefins consist essentially of one or more linear alpha-olefins.

8. The process of claim 5, wherein the olefin mixture contains less than 5% w of methyl-branched vinylidene olefins, calculated on the weight of ethyl- and higher alkyl-branched vinylidene olefins in the mixture.

9. The process of claim 2, wherein the olefin feedstock mixture contains one or more vinylidene olefins having carbon numbers in the range from about 10 to 20 and one or more non-vinylidene olefins having carbon numbers in the range from about 10 to 20.

10. The process of claim 5, wherein the olefin mixture contains less than 5% w of methyl-branched vinylidene olefins, calculated on the weight of ethyl- and higher alkyl-branched vinylidene olefins in the mixture.

11. The process of claim 1, wherein the temperature is in the range from about 40° to 275° C.

12. The process of claim 1, wherein the temperature is in the range from about 40° to 250° C.

13. The process of claim 1, wherein the temperature is in the range from about 50° to 200° C.

14. The process of claim 13, wherein step (a) is terminated prior to conversion of more than about 10% of the linear olefins.

15. The process of claim 14, wherein step (a) is terminated prior to conversion of more than about 5% of the linear olefins.

16. A process for the selective separation of ethyl- and higher alkyl-branched vinylidene olefins from their mixtures with linear olefins and for the preparation of alkyl esters of acrylic acids, which comprises steps for
    (a) contacting and reacting a liquid phase olefin feedstock mixture consisting essentially of one or more ethyl- and higher alkyl-branched vinylidene olefins having carbon numbers in the range from about 10 to 20 and one or more linear olefins having carbon numbers in the range from about 10 to 20 with one or more reactive agents selected from the group consisting of alkyl esters of acrylic acid having the formula

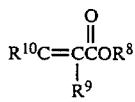

wherein $R^8$ is an alkyl group of from 1 to about 15 carbon atoms, $R^9$ is a hydrogen atom or an alkyl group of from 1 to about 4 carbon atoms, and $R^{10}$ is a hydrogen atom or an alkyl group of from 1 to about 18 carbon atoms, at a temperature of between about 10° and 300° C. and in the presence of a catalytically effective amount of one or more ene reaction catalysts, to selectively convert all or part of the ethyl- and higher alkyl-branched vinylidene olefins of said feedstock mixture to higher carbon number acrylic acid esters and to produce a product mixture comprising the resulting higher acrylic acid esters and unreacted olefins, (b) terminating step (a) prior to conversion of more than about 20% of the linear olefins by reaction with reactive agent, and (c) separating the unreacted olefins from the product mixture.

17. The process of claim 16, wherein the temperature is in the range from about 50° to 200° C. and step (a) is terminated prior to conversion of more than about 10% of the linear olefins.

18. The process of claim 17, wherein the temperature is in the range from about 50° to 200° C. and step (a) is terminated prior to conversion of more than about 5% of the linear olefins.

19. The process of claim 16, wherein the olefin mixture contains less than 5% w of methyl-branched vinylidene olefins, calculated on the weight of ethyl- and higher alkyl-branched vinylidene olefins in the mixture.

20. The process of claim 19, wherein the reactive agent comprises one or more alkyl esters of acrylic acid selected from the group consisting of methyl acrylate, ethyl acrylate, n-propyl acrylate, isopropyl acrylate, n-butyl acrylate, isobutyl acrylate, tertiary-butyl acrylate, n-octyl acrylate, isooctyl acrylate, 2-ethylhexyl acrylate, n-tetradecyl acrylate, n-hexadecyl acrylate, methyl alpha-chloroacrylate, trimethylolpropane triacrylate, 1,6-hexanediol diacrylate, and mixtures thereof.

21. The process of claim 20, wherein the temperature is in the range from about 40° to 250° C.

22. The process of claim 21, wherein the temperature is in the range from about 50° to 200° C.

23. The process of claim 22, wherein step (a) is terminated prior to conversion of more than about 10% of the linear olefins.

24. The process of claim 23, wherein step (a) is terminated prior to conversion of more than about 5% of the linear olefins.

25. A process for the selective separation of vinylidene olefins from their mixtures with linear olefins and for the preparation of alkyl esters of acrylic acids, which comprises steps for (a) contacting and reacting a liquid phase olefin feedstock mixture consisting essentially of (i) one or more $C_6$ to $C_{30}$ ethyl- and higher alkyl-branched vinylidene olefins and (ii) one or more $C_6$ to $C_{30}$ linear alpha-olefins with one or more reactive agents selected from the group consisting of methyl acrylate, ethyl acrylate, n-propyl acrylate, isopropyl acrylate, n-butyl acrylate, isobutyl acrylate, tertiary butyl acrylate, n-octyl acrylate, isooctyl acrylate, 2-ethylhexyl acrylate, n-tetradecyl acrylate, n-hexadecyl acrylate, methyl alpha-chloroacrylate, trimethylolpropane triacrylate, 1,6-hexanediol diacrylate, and mixtures thereof, at a temperature of between about 50° and 200° C. and in the presence of a catalytically effective amount of one or more ene reaction catalysts, to selectively convert all or part of the ethyl- and higher alkyl-branched vinylidene olefins of said feedstock mixture to higher carbon number acrylic acid esters and to produce a product mixture comprising the resulting higher carbon number acrylic acid esters and unreacted olefins, (b) terminating step (a) prior to conversion of more than about 20% of the linear olefins by reaction with reactive agent, and (c) separating the unreacted olefins from the product mixture.

26. The process of claim 25, wherein step (a) is terminated prior to conversion of about 10% of the linear olefins by reaction with reactive agent.

27. The process of claim 26, wherein the reactive agent is methyl acrylate.

28. The process of claim 27, wherein step (a) is terminated prior to conversion of about 5% of the linear olefins by reaction with reactive agent.

29. The process of claim 26, wherein the one or more ene reaction catalysts are selected from the group consisting of aluminum chloride, indium chloride, and $C_1$ to $C_4$ aluminum dichlorides.

30. The process of claim 29, wherein the ene reaction catalyst comprises ethyl aluminum dichloride.

31. The process of claim 28, wherein the one or more ene reaction catalysts are selected from the group consisting of aluminum chloride, indium chloride, and $C_1$ to $C_4$ aluminum dichlorides.

32. The process of claim 31, wherein the ene reaction catalyst comprises ethyl aluminum dichloride.

* * * * *